US008628807B2

(12) United States Patent
Van Dijk et al.

(10) Patent No.: US 8,628,807 B2
(45) Date of Patent: Jan. 14, 2014

(54) NEGATIVELY CHARGED POLYSACCHARIDE DERIVABLE FROM ALOE VERA

(75) Inventors: Willem Van Dijk, Amstelveen (NL); Annelize Frieda Goedbloed, Delft (NL); Floris Jan Robbert Koumans, Delft (NL)

(73) Assignee: 2QR Research B.V., Delft (NL)

( * ) Notice: Subject to any disclaimer, the term of this patent is extended or adjusted under 35 U.S.C. 154(b) by 190 days.

(21) Appl. No.: 10/500,390

(22) PCT Filed: Dec. 23, 2002

(86) PCT No.: PCT/NL02/00868
§ 371 (c)(1),
(2), (4) Date: Sep. 14, 2004

(87) PCT Pub. No.: WO03/055918
PCT Pub. Date: Jul. 10, 2003

(65) Prior Publication Data
US 2005/0019433 A1    Jan. 27, 2005

(30) Foreign Application Priority Data
Dec. 27, 2001 (EP) .................................. 01205253

(51) Int. Cl.
*A61K 8/73* (2006.01)

(52) U.S. Cl.
USPC ............. 424/744; 424/725; 424/59; 424/400; 424/401

(58) Field of Classification Search
None
See application file for complete search history.

(56) References Cited

U.S. PATENT DOCUMENTS

| 3,103,466 | A |   | 9/1963  | Farkas                     |
|-----------|---|---|---------|----------------------------|
| 3,360,511 | A |   | 12/1967 | Farkas                     |
| 4,315,918 | A | * | 2/1982  | Gayst et al. ........ 514/21 |
| 4,861,761 | A | * | 8/1989  | Madis et al. ........ 514/54 |
| 5,824,659 | A | * | 10/1998 | Strickland et al. ... 514/54 |
| 5,902,796 | A | * | 5/1999  | Shand et al. ........ 514/54 |
| 6,133,440 | A | * | 10/2000 | Qiu et al. .......... 536/123 |
| 6,290,964 | B1|   | 9/2001  | Shupe et al.               |
| 6,395,311 | B2| * | 5/2002  | Jia .................. 424/744 |
| 6,482,942 | B1| * | 11/2002 | Vittori ............... 536/128 |
| 2002/0071868 | A1| * | 6/2002 | Jia .................. 424/486 |

OTHER PUBLICATIONS

Meglasson, Mannose Phosphorylation by gluokinase from liver and transplantable insulinoma. 1983, Diabetes, 32, p. 1146-1151.*
Wang et al., A Study of Polysaccharides in Aloe, 1989, Acta Botanica Sinica, vol. 31, pp. 389-392.*
http://www.thegardenhelper.com/aloe~vera.html.*
Yaron et al., Stabilization of Aloe vera gel by Interaction with SUlfated Polysaccharides from Red Microalgae and with Xanthan Gum, 1992, J Agric Food Chem, 40: 1316-1320.*
Ro et al., Inhibitory Mechanism of Aloe Single Component (Alprogen) on Mediator Release in Guinea Pig Lung Mast Cells Activated with Specific Antigen-antibody Reactions, 2000, J Pharm Exper Therap, 292: 114-121.*
Vilkas et al., The glucomannan system from *Aloe* vahombe (liliaceae). III. Comparative studies on the glucomannan components isolated from the leaves, 1986, Biochimie, 68: 1123-1127.*
Hart et al., An Anti-Complementary Polysaccharide with Immunological Adjuvant Activity from the Leaf Parenchyma Gel of *Aloe vera*, 1989, Planta Medica, 55: 509-512.*
Antoni Femenia et al.:, "Compositional features of polysaccharides from *Aloe vera* plant tissue.", Carbohydrate Polymers, vol. 39, 1999, pp. 109-117, XP002199218 p. 113; table 4.
E. Roboz et al.:, A mucilage from *Aloe vera*:, The Journal of the Americal Chemical Society, vol. 70, Sep. 1, 1948, pp. 3248-3249, XP002199219 p. 3248, left-hand column, paragraph 2.
Chemical Abstracts, vol. 129, No. 21, Nov. 23, 1998 Columbus, Ohio, US; abstract No. 271794s, Shin Kuk Hyun: "Effects of high molecular weight fractions of Aloe spp. on alcohol metabolism" XP002237952 abstract & Saengyak Hakhoechi, vol. 29, No. 2, 1998, pp. 120-124.

* cited by examiner

*Primary Examiner* — Patricia Leith
*Assistant Examiner* — Catheryne Chen
(74) *Attorney, Agent, or Firm* — Young & Thompson

(57) ABSTRACT

A new composition of matter is provided comprising negatively charged polysaccharides which can be derived from *Aloe vera* and a process to prepare that composition of matter by sub fractionation of an extract of *Aloe vera*, passing the formed subfraction over a positively charged column and eluting the same with a salt solution. Optionally the *Aloe vera* is pre purified over a Sephadex G-25 column. This composition of matter and also the extract comprising the same which is formed after pre purification or ultra filtration of an *Aloe vera* extract is useful as a food supplement or in dietary foods, for use in personal care and in cosmetics, especially to prevent an infection with the bacteria *Helicobacter pylori, Pseudomonas aeruginosa, Streptococcus mutans* or *Streptococcus sanguis*.

12 Claims, 4 Drawing Sheets

Figure 1:
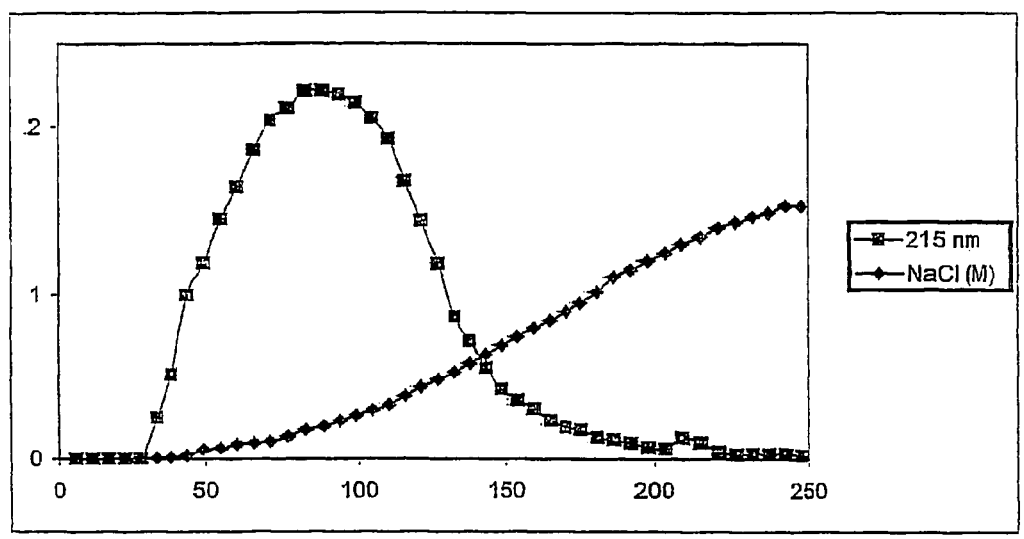

Adherence of *H. pylori* to human antrum slices (magnification 200x). *a.* regular view. *b.* AV5-I; *c.* AV5 I-D0.

NEGATIVELY CHARGED POLYSACCHARIDE DERIVABLE FROM ALOE VERA

The present invention relates to a composition of matter comprising polysaccharides derivable from *Aloe vera* and a method to prepare said composition of matter, a plant or animal extract comprising said composition of matter and a method to prepare said plant or animal extract and the application thereof as food supplement, in personal care and in pharmaceutical use.

*Aloe* is a member of the lily family comprising over two hundred different *Aloe* species. *Aloe barbadensis* Miller or *Aloe Curacao* is generally recognized as the "true *aloe*" because of its wide use and most effective healing power. *Aloe vera* contains two major liquid sources, a yellow latex (exudate) and the clear gel (mucilage). The mucilaginous jelly from the parenchymal cells of the plant is referred to as *Aloe vera* gel. *Aloe vera* gel is about 98.5% water by weight. More than 60% of the total solid is made up of polysaccharides of carbohydrate origin.

Since the earliest days of recorded history man has made use of whole leaves, exudates and fresh gels obtained from *Aloe vera* because it is responsible for a range of biological activities including antibacterial, antiviral and anti-inflammatory activities. It was the traditional medicine of many cultures and used inter alia for leprosy, burns and allergic conditions. Other *Aloe* species with healing power are for instance *Aloe arborescens*, *Aloe vahombe*, *Aloe ferox* and *Aloe saponaria*.

In the literature a lot of different polysaccharides mentioned to be responsible for said biological activities have been described. For instance in U.S. Pat. No. 4,861,761 a one-step method for the preparation of a pure therapeutically active polysaccharide called Aloeferon with a molecular weight of about 70 kD has been disclosed.

In U.S. Pat. No. 5,118,673 said biological activities are ascribed to Acemannan, a polysaccharide extracted from *Aloe vera* gel comprising marmose molecules which are for about 91% O-acetylated. Besides mannose another glysosyl component namely galactose is present in a ratio of about 20:1. The molecular weight is on the average about 1000 kD. This non-toxic polymer is also said to be effective in the suppression of tumours.

However, recently Nirmal Pugh et al. described in the Journal of Agricultural Food Chemistry, 49, 1030-1034 (2001) a new high-molecular-weight polysaccharide from *Aloe vera* with potent immuno stimulatory activity. The molecular weight is reported to be 4000-5000 kD. The major glycosyl components are glucose (37.2%), galactose (23.9%), mannose (19.5%), and arabinose (10.3%). It is stated that although this polysaccharide comprises only 0.015% of the original dry weight, its biological activity in this assay accounts fully for the activity in the crude *Aloe* juice. It is proposed that the much lower immuno stimulatory activity of acemannan is due to a very potent substance (most likely Aloeride polysaccharide) that is present in trace amounts as a "contaminant".

Therefore, up to now it has not been established for sure which fraction of *Aloe vera* causes the biological activity of said plant. An object of the present invention is to isolate a novel composition of matter derivable from *Aloe vera* or a plant or animal extract which is suitable as food supplement or in dietary foods, in personal care or in cosmetics, or in pharmaceutical use, especially to prevent the adhesion of microorganisms in tissues. Another object of the invention is to provide processes by which such a composition of matter or extract may be isolated.

It was found that a new negatively charged polysaccharide fraction isolated from *Aloe vera* and mainly comprising mannose showed a surprisingly higher biological activity than the corresponding not charged or only weakly charged polysaccharide fractions, which fractions do not bind to a positively charged column. This higher biological activity has been found for subfractions with all apparent molecular weights.

The present invention provides such a composition of matter comprising polysaccharides derivable from *Aloe vera* with the following characteristics: a) the polysaccharides comprise 70-90% D-mannose with a range between 60-100%, 30-10% D-glucose with a range between 40-0% and 0-10% other monosaccharides, b) the polysaccharides are negatively charged and c) the polysaccharides bind to a positively charged column. With the second indicated broader range is meant that a polysaccharide with a weight percentage of indicated monosaccharides within the broad ranges belong to the scope of the invention, but that those with such a weight percentage within the small ranges are preferred. All percentages relating to a composition of matter relate to weight percentages.

Preferably, in said composition of matter the polysaccharides have an average molecular weight of about 100-300 kD. However as also other subfractions with an average molecular weight of either 10-50 kD, or 50-100 kD or higher than 300 kD show a considerable biological activity, these subfractions also form an aspect of the present invention. Preferably, the ratio of D-mannose and D-glucose in said polysaccharides is within the range of about 5 to 20, preferably 7-10.

The present invention also provides a process to prepare said composition of matter by the following process steps:
a) sub fractionation of a plant or animal extract, for instance an *Aloe* or *Aloe vera* extract in two fractions, one with an apparent molecular weight of >±5 kD, named subfraction I and one with an apparent molecular weight of <±5 kD
b) passing of subfraction I over a positively charged column as for instance a DEAE-Sepharose column, a DEAE-Sephadex column or a DEAE-cellulose column,
c) eluting the part of subfraction I bound to said column with a salt solution, for instance with a sodium chloride solution resulting in subfraction I-D$_I$
d) desalting and ultra filtration of I-D$_I$, for instance through a PM10 membrane under nitrogen pressure, to concentrate I-D$_I$ to about 0.1 of the original volume of the *Aloe vera* extract
e) optionally preparation of subfractions of I-D$_I$ with desired apparent molecular weights of >300 kD, 100-300 kD, 50-100 kD and 10-50 kD, particularly by sequential ultra filtration over a XM-300, XM-100, XM-50 and finally a PM-10 membrane or by preparative FPLC over a Superose column.

Preferably, a pre purification step is carried out before process step "a" over a Sephadex G-25 column.

In an article of A. Femenia et al., Carbohydrate Polymers 39, 109-117 (1999), also extracts of *Aloe vera* have been described, however said extracts are not further fractionated and not further separated with the aid of a positively charged column.

The present invention also provides as a suitable substance a plant or animal extract, especially an *Aloe* extract, more especially being an extract from *Aloe vera*, indicated as NAG-25 (no affinity for Sephadex G-25) extract, which comprises the composition of matter as defined above in a concentration of 5-10, especially 8 times higher and of low molecular weight compounds of about 2 times lower than the extracts known in the art. Generally such a plant or animal NAG-25 extract (to be understood as plant NAG-25 or animal NAG-25 extract) will be a sap.

According to a further aspect of the invention a process has been provided to prepare such a plant or animal NAG-25 extract by purification of the corresponding untreated plant or animal extract over a Sephadex G-25 column to remove materials with affinity for said column. By "corresponding" is meant the same species of plant or animal. Such a NAG-25 extract comprises all high molecular compounds without any affinity for the polysaccharide matrix of the positively charged column used but also less low molecular weight compounds than expected. If necessary the resulting extract is further concentrated by a factor of 5 to 50 by the removal of water resulting in the plant or animal NAG-25 extract according to the present invention, also indicated with 2QRide. Generally, if the starting compound is a spray dried powder a concentrated solution may be obtained by starting in a low volume of water in which case no further concentrating steps are necessary.

Preferably, if a plant is used to prepare the composition of matter or the NAG-25 extract according to the invention this is an *Aloe* plant, especially an *Aloe vera*. However an extract containing the negatively charged polysaccharides can also be gained from other plants. Biologically active polysaccharides have been found in *Vaccinnium macrocarpon* (Cranberry), *Panax ginseng, Plantago, Echinacea, Garcinia, Arnica, Angelica, Hibiscus, Glycyrrhiza, Morinda* etc. If an animal is used especially fishes and slugs are suitable. However besides extracts from plants and animals also extracts of lower organisms like seaweed, sponges and mushrooms should be considered for this patent application as belonging to the scope of the invention. Therefore for this patent application the wording plant and animal also comprise lower organisms.

According to still a further aspect of the invention an *Aloe* extract, especially an *Aloe vera* extract is provided which has been ultra filtrated preferably with a cross flow method over a membrane to prepare subfractions with a desired apparent molecular weight as indicated above, but with both charged and uncharged polysaccharides, binding and not binding to a positively charged column. Also this *Aloe* ultra filter extract comprises the new negatively charged polysaccharides according to the invention. Preferably, said charged and uncharged polysaccharides are farther separated in charged and uncharged polysaccharides by passing over charged filters, from which the charged polysaccharides are indicated with 2QRide.

The new negatively charged polysaccharides, the plant or animal NAG-25 extracts and the *Aloe* ultra filter extract comprising a high percentage of said negatively charged polysaccharides according to the invention herein described have a high biological activity and may be applied as food supplement or in dietary foods, for instance to prevent the adhesion of bacteria, particularly in the mucous layer of the human gastric epithelium. Furthermore, said negatively charged polysaccharides, the plant or animal NAG-25 extracts and the *Aloe* ultra filter extracts comprising the same can be applied for personal care and cosmetic use to prevent infections of detrimental and harmful microorganisms, for instance in dental care as in toothpaste to prevent *gingivitis* and *caries*. Furthermore, the charged polysaccharides and said extracts comprising the same can probably suitably be applied in liquids for instance to protect eye lenses, in sprays and tonics, and in drops, creams and gels to look after the skin, hair, eyes and ears. Finally, said polysaccharides and said extracts comprising the same are to be applied in pharmaceutical use, especially as a medicament or adjuvans in a pharmaceutical composition to prevent or cure infections with infectious microorganisms like viruses, fungi and bacteria or in prevention and healing of inflammations, and probably in immuno therapy and in wound healing. An infection with four of said bacteria, the *Helicobacter pylori, Pseudomonas aeruginosa, Streptococcus mutans* and *Streptococcus sanguis* bacteria, can particularly be combatted by these polysaccharides.

Throughout this patent application all percentages relating to a composition of matter relate to weight percentages. Furthermore, by "corresponding" is meant as starting material the same species of plant or animal as the resulting extract. Furthermore, unless otherwise indicated, by "extract" is meant extract by water.

The infection of the stomach by *Helicobacter pylori* is one of world's most common bacterial infections. A minority of infected individuals develops a gastro duodenal disease associated with said bacterium. Examples thereof are the development of peptic ulcer disease, chronic and atrophic gastritis mucosa-associated lymphoid tissue lymphomas and gastric cancer. Adhesion of *Helicobacter pylori* to the mucosa is limited to the apical surface of the mucosa epithelial cells and to cells lining the gastric pits, particularly in the bottom part of the stomach. Different adhesins have been found to mediate this binding, by recognition of proteins or specific glycoconjugates, i.e. mucins, present on the eukaryotic cell surface (D. Ilver et al., Science 279, 373-377 (1998)). Therefore, at least part of the adhesion of *Helicobacter pylori* seems to be glycoconjugate dependent. However until now the effectivity of a plant NAG-25 or animal NAG-25 extract, as for instance an Aloe extract or an ultra filtration *Aloe* extract containing negatively charged polysaccharides according to the invention to combat an infection with *Helicobacter pylori* has nowhere been described.

In an established ELISA assay it appeared that *Aloe vera* extracts could inhibit the adhesion of preparations of *Helicobacter pylori* adhesins to salivary mucins indeed. Therefore it was decided to investigate which components in the extract are responsible for the inhibition. Active subfractions of *Aloe vera* gels were obtained by a combination of precipitation, molecular sieving and anion-exchange chromatography and were characterized with regard to molecular weight and sugar composition and appeared to be novel.

The present invention is illustrated by the following figures with the legends:

FIG. 1: Elution of the bound fraction of 200 ml AV-15 fraction I (the >5 kD fraction of AV-15 NAG) from a DEAE-Sepharose column with a NaCl gradient from 0-2 M NaCl. The Y-axis represents the NaCl concentration (M) as well as the absorbance at 215 nm; the X-axis represents the elution volume. Zero ml represents the starting point of the 0-3.0 M NaCl gradient which was applied after collection of the DEAE-unbound AV-D$_0$ fraction followed by washing the column with 2 column volumes of Milli-Q water.

Figure 2:
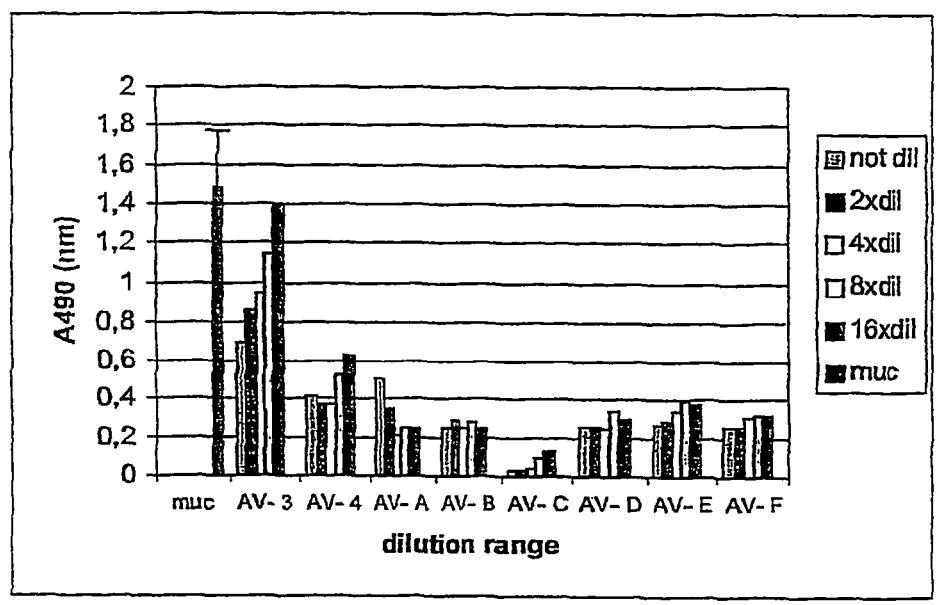

FIG. 2: Inhibition of adherence of mucin to *Helicobacter pylori* S-layer by *Aloe vera* extracts obtained from various sources with muc, positive control containing mucine only AV, co-incubation of mucine with a 2-16 fold dilution range of *Aloe vera* extract AV-3 and AV-4 1:1 *Aloe* Gel products; AV-B, AV-D, AV-E and AV-F are commercially available *Aloe vera* sources concentrated 40, 10, 5 and 2.5 times respectively $A_{490\ nm}$ absorbance values per well in duplo, for mucin in quattro.

Figure 3:
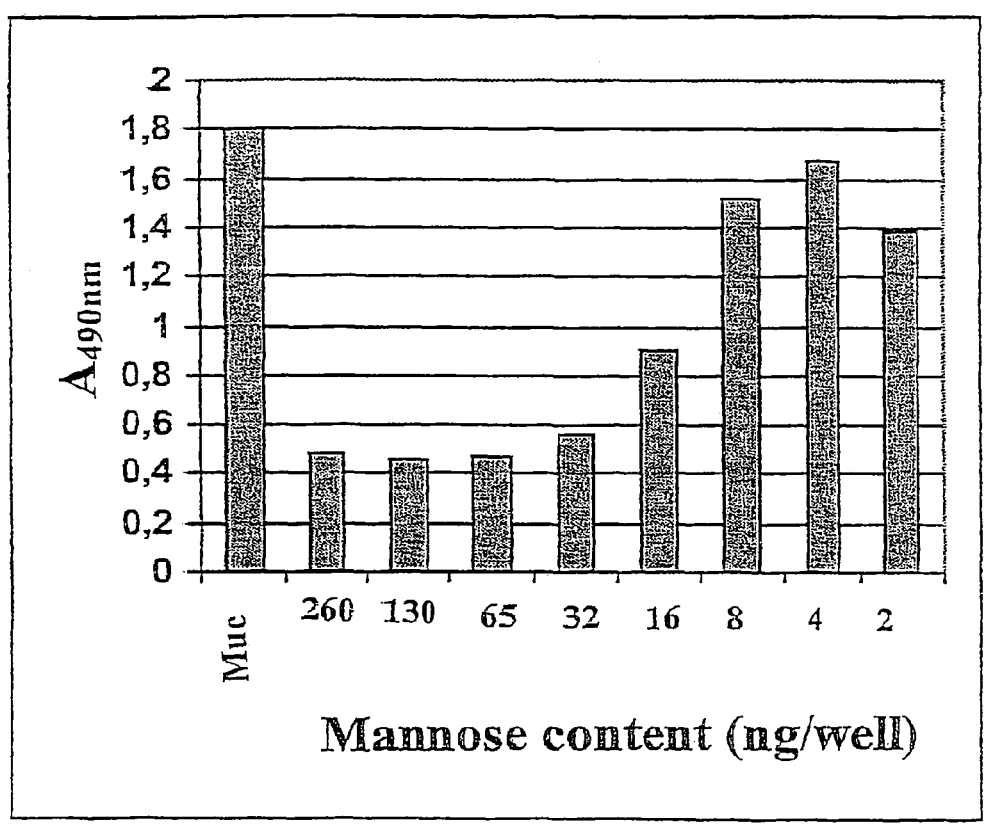

FIG. 3: Inhibition of 100-300 kD subfraction of charged fraction I-D$_I$ of an *Aloe vera* extract with
  muc, positive control containing mucine only
  AV-2, an 1:1 *Aloe*-Gel product in different concentrations
  A$_{490\,nm}$ absorbance values per well in duplo, for mucin in quattro.

Figure 4:

FIG. 4: Inhibition of adherence of FITC-labeled *Helicobacter pylori* to human antrum slices by subfractions of *Aloe vera* extract AV-5 with
  a. regular view
  b. consecutive slice incubated with FITC-labeled *Helicobacter pylori* and total fraction I
  c. consecutive slice incubated with FITC-labeled *Helicobacter pylori* and fraction I-D$_0$, identical with controls without *Aloe vera* subfractions.

The following abbreviations used throughout this patent application have the meaning:
DEAE=diethylaminoethyl
FITC=fluorescein 5-isothiocyanate
HPAEC-PAD=high pH anion-exchange chromatography with pulsed amperometric detection
BCA=bicinchoninic acid
ELISA=enzyme-linked immunoassay
A$_{490\,nm}$=absorbance at 490 nm
NMR=nucleic magnetic resonance A DEAE-binding fraction can be isolated from the >5 kD fraction I of AV-15 NAG-25 by DEAE-Sepharose, DEAE-cellulose and DEAE-Sephacel chromatography under elution with 0.5 or 1 M NaCl. This is exemplified by the NaCl gradient in FIG. 1 for the elution of the DEAE-binding fraction of 200 ml AV-15 fraction I. Non-specific adhesion to the polysaccharide matrix is unlikely since the NAG-25 fraction and not the *Aloe* gel is used as a starting material for the subfractionation. Therefore the NaCl-dependent elution confirms that the DEAE-binding is caused by a negative charge on the molecules. Proteins or peptides were below detectable levels. Sugar analysis revealed that galacturonic acid is present in small amounts, but this sugar appeared also to be present in the non-binding D$_0$ fraction (results not shown). So the molecular nature of the negative charge is not known yet.

All available *Aloe vera* extracts inhibited the interaction with the mucins in a dose-dependent way when they were co-incubated with a fixed concentration of mucin, see FIG. 2. Variations in inhibitory activity reflect differences in compositions of extracts in dependence of source or culture conditions of the *Aloe vera* plant but do hardly change the proportional biological activity of the various subfractions. Apparently an *Aloe vera* component or *Aloe vera* components compete with mucin for the binding to the *Helicobacter pylori* adhesin preparation.

The majority of the inhibitory activity of the *Aloe vera* extracts appear to reside in a subfraction, I, with a molecular weight of at least 5 kD, according to its behaviour on Sephadex G-25 chromatography. Further studies were focussed on this charged fraction because of its high activity. Carbohydrate analysis and analytical permeation chromatography on a Superdex HR-200 column revealed that polysaccharides were the major components. The sugar composition depends on the *Aloe vera* extract but any extract consists of homo- and hetero polymers of mannose and glucose.

The bulk of the inhibitory activity could be retained and eluted specifically with NaCl from anion-exchange columns. DEAE-Sepharose chromatography was applied to isolate this apparently negatively charged polysaccharide fraction, indicated with fraction I-D$_L$. Sequential ultra filtration was employed to obtain subfractions with apparent molecular weights of >300 kD, 100-300 kD, 50-100 kD and of 10-50 kD. These subfractions were also prepared for the components that did not bind to DEAE-Sepharose indicated with fraction I-D$_0$. All subfractions appear to contain for 90%, or particularly for 95% or more homo- or hetero polymers of mannose and glucose, of which the polymannoses form the major components as summarized in table 1 here below. The remainder comprises galactose and various non-identified sugars (not shown in the table).

As is shown in table 1, the inhibitory activities of the DEAE-binding fractions are considerably higher than of the non-binding subfractions of the *Aloe vera* extract. The 100-300 kD subfraction of I-D$_I$ expresses the highest inhibitory activity (82%), although in the assay per well, viz. 12.5 µl, only a low amount of *Aloe vera* polysaccharide is present, nl. 0.325 µg of mannose and 0.045 µg of glucose. This represents about 9.3 nM of polysaccharide in the 200 µl end volume assuming a mean molecular weight of 200 kD. The inhibition is dose-dependent and 50% of the inhibition is reached at a 10-fold lower concentration of about 0.03 µg of mannose per well or about 0.9 nM of polysaccharide, see FIG. 3. The very low amount of composition of matter recovered in the >300 kD DEAE-binding fraction is also very active per pmol of polymannose when the high molecular weights have been taken into account. The other two DEAE binding fractions show a much lower specific activity but still higher than in the corresponding subfractions of the DEAE non-binding I-D$_0$. Remarkably, no inhibitory activity was detectable for the polysaccharides present in fraction I-D$_0$ with molecular weights >300 kD.

TABLE 1

Inhibitory activity of subfractions I-D$_0$ and I-D$_I$ on the adherence of *H. pylori*

| | Inhibition of mucin binding (%) | | Sugar composition (µg/ml) | | | | | |
|---|---|---|---|---|---|---|---|---|
| | | | I-D$_0$ | | | I-D$_1$ | | |
| Subfraction | I-D$_0$ | I-D$_1$ | Man | Glc | Ratio | Man | Glc | Ratio |
| 10-50 kD | 27 | 64 | 696 | 266 | 2.6 | 132 | 22 | 6.0 |
| 50-100 kD | 17 | 43 | 77 | 7 | 11 | 21 | 4 | 5 |
| 100-300 kD | 37 | 82 | 20 | 1.6 | 12.5 | 26 | 3.6 | 7.2 |
| >300 kD | n.d. | 52 | 9.4 | 9 | 1 | 4.6 | 1.7 | 2.7 |

Subfractions of *Aloe vera* extract AV-2 (see Materials) are prepared by sequential ultrafiltration starting from 25 ml of said extract AV-2. The volume of each subfraction is adjusted to 12.5 ml. The data are based on values in duplo obtained for equal amounts (12.5 µl) of each fraction and are expressed relative to the absorbance measured in the control wells containing mucin only. The inhibitory activity of 12.5 µl of the original AV-2 extract with 813 µg glucose/ml and 325 µg mannose/ml, viz. 286 nM of polysaccharide, was 76%.

Inhibition of binding of *Helicobacter pylori* to gastric mucosa was demonstrated by incubating sequential slices of human antrum mucosa with FITC-labelled *Helicobacter pylori* in the absence and presence of *Aloe vera* subfractions. Like in the study of Boren et al., Science, 262, 1892-1895 (1993), selective binding of FITC-labeled *Helicobacter pylori* cells was only observed on the mucosal linings of the antrum, see FIGS. 4a and 4c. Co-incubation of the FITC-labelled *Helicobacter pylori* with the total weight fraction I, viz. I-D$_0$ and I-D$_I$ fractions of an *Aloe vera* extract strongly inhibited the adherence of the bacteria to the mucosa (see FIG. 4b) with is in sharp contrast with the absence of inhibition when subfraction I-D$_0$ alone was co-incubated. This is another strong indication that the inhibitory activity resides in the negatively charged fraction.

A comparable inhibition pattern has been found for Syto-13 labeled *Helicobacter pylori* wherein Syto-13 is a green fluorescent stain applying two different concentrations of *Aloe vera* subfractions according to the invention on MUC5-labelled multi-well plates. In an article from Van den Brink et al., Gut 46, 601-607 (2000), "*H. pylori* co localizes with MUC-5AC in the human stomach" it has been described that *H. pylori* in the stomach binds to a specific mucin present on the antrum part of the stomach. Therefore, the effect of *Aloe vera* subfractions on similar salivary mucin in an in vitro assay system can be used as a model for the mucin-specific attachment of *H. pylori* to the epithelium of the stomach.

The results are shown in the tables 2 and 3.

TABLE 2

Inhibitory activity of subfraction I-$D_I$ of an AV extract on the adherence of *H. pylori*

| Expt. 1 MUC-5 (dilution range) | Fluorescence (arbitrary units) | | Inhibition (%) |
|---|---|---|---|
| | *H. pylori* | *H. pylori* + 0.010 ml AV-17 I-$D_I$ fraction | |
| 1 | 4572 | 2304 | 50 |
| 3 | 4195 | 1956 | 53 |
| 9 | 1904 | 353 | 81 |
| 27 | 650 | 89 | 86 |
| 81 | 346 | 129 | 73 |

TABLE 3

Inhibitory activity of subfraction I-$D_I$ of an AV extract on the adherence of *H. pylori*

| Expt. 2 MUC-5 (dilution range) | Fluorescence (arbitrary units) | | Inhibition (%) |
|---|---|---|---|
| | *H. pylori* | *H. pylori* + 0.025 ml AV-17 I-$D_I$ fraction | |
| 1 | 3308 | −38 | 100 |
| 2 | 3627 | 59 | 97 |
| 4 | 2666 | 32 | 98 |
| 8 | 1679 | 58 | 96 |
| 16 | 1388 | 65 | 95 |
| 32 | 968 | 107 | 89 |

In the same way the effect of the adherence of an *Aloe vera* subfraction according to the invention on two Syto-13 labeled strains of *P. aeruginosa* was tested on MUC5-labelled multi-well plates. The amount of bacteria bound to the plates was dependent on the amount of coated MUC-5. The results are given in table 4 and table 5, respectively.

TABLE 4

Inhibitory activity of subfraction I-$D_I$ of an AV extract on the adherence of *P. aeruginosa*

| | MUC-5 (1:50) | | MUC-5(1:100) | |
|---|---|---|---|---|
| Condition | Arb. Units | % inhib. | Arb. Units | % inhib. |
| PA025 | 19630 | 0 | 9800 | 0 |
| PA025 + AV-16-$D_I$ | 4438 | 77 | 1103 | 89 |

TABLE 5

Inhibitory activity of subfraction I-$D_I$ of an AV extract on the adherence of *Pseudomonas aeruginosa*

| | MUC-5 (1:50) | | MUC-5 (1:100) | |
|---|---|---|---|---|
| Condition | Arb. Units | % inhib. | Arb. Units | % inhib. |
| PA14 | 24450 | 0 | 6050 | 0 |
| PA14 + AV-16-$D_I$ | 9857 | 60 | 1103 | 82 |

In the same way the effect of the adherence of an *Aloe vera* subfraction according to the invention on a Syto-13 labeled strain of *Streptococcus mutans* and on a Syto-13 labeled strain of *Streptococcus sanguis* was tested on agglutinin-enriched saliva coated to the plates. The amount of bacteria bound to the plates was dependent on the amount of coated MUC-5. The results are given in table 6 and table 7, respectively.

TABLE 6

Inhibitory activity of subfraction I-$D_I$ of an AV extract on the adherence of *Streptococcus mutans*

| | Agglutinin conc. | | Agglutinin 2xdil. | |
|---|---|---|---|---|
| Condition | Arb. Units | % inhib. | Arb. Units | % inhib. |
| *S. mutans* | 3995 | 0 | 1903 | 0 |
| *S. mutans* + AV-16-DI | 947 | 76 | 869 | 55 |

TABLE 7

Inhibitory activity of subfraction I-$D_I$ of an AV extract on the adherence of *Streptococcus sanguis*

| | Agglutinin conc. | | Agglutinin 2xdil. | |
|---|---|---|---|---|
| Condition | Arb. Units | % inhib. | Arb. Units | % inhib. |
| *S. sanguis* | 24022 | 0 | 14216 | 0 |
| *S. sanguis* + AV-16-D1 | 9921 | 59 | 8240 | 43 |

It will be appreciated by the person skilled in the art that the anti adhesive polysaccharides according to the invention are anti infectiva against all microorganisms which invade the surface of the host tissue which are exemplified by the *Helicobacter pylori, Pseudomonas aeruginosa, Streptomyces mutans* and *sanguis* bacteria as mentioned above. Except of bacteria invasion is a phenotype common to cancer cells, leukocytes, parasites, bacteria and viruses involving cell-cell adhesion, cell-matrix adhesion, proteolysis and motility. These activities are regulated by the cross talk between invaders and host. The adhesion of microorganisms to the surface of the host tissue is often the first step in pathogenesis. Increasingly the patient population becomes highly susceptible to morbidity and mortality associated with drug resistant pathogens. Inhibition of adhesion is therefore an important property of new anti infectiva.

The polysaccharides according to the invention reduce the biofilm load. This is due to a reduction in adhesion of Gram negative and probably also of Gram positive bacteria to the cells. Furthermore, said polysaccharides also interfere with the adhesive processes of viruses, fungi, flagellates and other parasites and can be part of a therapy to treat or prevent affections and diseases of the whole body of both humans, animals and possibly plants. Said polysaccharides which consist of simple monosaccharides are not expected to be toxic both in oral, topical, injectable and systemic applications.

Relating to the application of the negatively charged polysaccharides or plant or animal NAG-25 extracts comprising said polysaccharides according to the present invention in oral form, all suitable dosage forms applicable such as injectable fluids or tablets optionally comprising suitable excipients such as a cellulose product as for instance a microcrystalline or microfine cellulose or silica, disintegrants as for instance modified starches, sodium carboxy methyl cellulose or cross-linked poly vinyl pyrrolidone, optionally lubricants and optionally sweetenings agents like flavours and aromas, form an aspect of the present invention. Also other oral dosage forms like capsules and syrups optional together with suitable excipients comprising the polysaccharides of the present invention form an aspect thereof. However, said oral dosage forms can also be applied as a medicament in prevention or healing of an infection with infectious microorganisms or in prevention and healing of inflammations. Furthermore, also topical dosage forms like creams or gels form an aspect of the present invention, especially in the field of personal care or for cosmetic use.

Examples of affections, infections and diseases which can be prevented and treated by the anti adhesive polysaccharides of the present invention are besides those caused by microorganisms which invade the gastro-intestinal tract like the stomach by for instance *Helicobacter pylori* those of the:

skin, caused by
    *Staphylococcus aureus* and *Staphylococcus epidermitis* which are common pathogens, e.g. in hospitals
    viruses such as Kaposi' sarcoma-associated herpes virus, *herpes simplex* virus
    fungi such as *candida* sp., *Blastomyces dermatidis;* adhesion to the skin also includes adhesion to dermal microvascular endothelial cells eyes, caused by
    *Staphylococcus epidermitis* which plays an important role in the pathogenesis of some forms of endophthalmitis occurring after cataract surgery
    *Moraxella bovis* as the source of infectious bovine *keratoconjunctivitis* ear, nose and throat, caused by
    *Staphylococcus aureus* which adheres to the skin and mucous tissues
    bacteria involved in Otitis media and nasopharyngal infections such as *Haemophilus influenza, Streptococcus pneumoniae* and *Moraxella catarrhalis* the oral cavity, wherein the dental plaque biofim plays a pivotal role in the progression of dental diseases and polysaccharides are of great importance in the ecology of the dental biofilm, caused by
    bacteria involved in *caries* such as *Streptococcus sobrinus* as acariogenic strain, *Streptococcus mutans, Streptococcus salivarius, Streptococcus gordonii* and *Actinomyces viscosus, Actinobacillus actinomycetemcomitans*
    periodontopathogenic bacteria such as *Porphyromonas gingivalis* and *Streptococcus salivarius, Streptococcus oralis, Fusobacterium nucleatum* and *Prevotella intermedia*
    all oral *spirochetes* which are classified in the genus *Treponema,* such as *denticola, pectinovorum, socranskii* and *vincentii,*
    *Mycoplasma salivarium*
    microorganisms involved in nasal polyposis
    microorganisms involved in *Sinusitis* the urogenital tract, caused by
    gram negative *Uropathogenic Escherichia coli* which adhere to the tissues of the urogenital tract
    *Mycoplasma genitalium*
    *Trichomonas vaginalis*
    *Candida* species
    *Neisseria gonorrhoeae* adhesion to oviductal epithelium
    *Treponema pallidum* which is involved in *perivasculitis,* endothelial cell abnormalities that are prominent histopathologial features of syphilis and various cutaneous lesions that are the main clinical features of syphilis
    *Escherichia coil*
    *Citrobacter* species the gut, caused by
    *Salmonella* species e.g. *Salmonella typherium*
    *Proteuts mirabilis*
    *Clostridium* species, e.g. *difficile, perfringens, bifermentans*
    *Shigella* species, e.g. *flexneri*
    *Mycoplasma* species, e.g. *gallisepticum*
    *Enterococcus* species
    *Bacteroides fragilis*
    *Bacillus* species
    *Listeria monocytogenes*
    *Hepatitis* A virus
    *Campilobacter jejuni*
    *Salmonella typhimurium*
    *Yersina enterocolitica* and *Yersina pseudotuberculosis*
    *Aeromonas veronii biovar sobria*
    *Erwinia chrysanthemi* which is a model plant pathogen that has the potential to parasitize mammalian hosts as well as plants the respiratory tract caused by
    *Pseudomonas aeruginosa,* a gram-negative facultative pathogen of the bronchii and the lung as well as cystic in fibrosis patients
    *Klebsiella pneumoniae*
    *Bordetella* species, *pertussis, parapertussis* and *bronchiseptica*
    bacteria of the genus *Legionella* are intracellular parasites and major human pathogens
    the respiratory syncytical virus (RSV) which causes potentially lower respiratory tract infection in children
    *Mycoplasma pneumoniae*
    *Rhinovirus* which potentiates induction of proasthmatic changes
    *Cryptococcus neoformans* which usually occurs in the lungs, and is involved in interactions between yeasts and alveolar epithelial cells
    *Streptococcus* species such as *pyogenes* or *gordonji*
    *Escherichia pneumoniae,* an important respiratory pathogen
    the *Burkholderia cepacia* complex which consists of at least five well-documented bacterial genomovars, each of which has been isolated from the sputum of different patients with cystic fibrosis
    *Mannheimia (Pasteurella) haemolytica* which is one of the most important respiratory pathogens of domestic ruminants and causes serious outbreaks of acute pneumonia in neonatal, weaned and growing lambs, calves and goats. It is also an important cause of pneumonia in adult animals
    *Rhinotracheitis* virus, parainfluenza-3 virus or bovine respiratory syncytial virus which predispose animals to *M. haemolytica* infection the organs, blood, lymph, bloodvessels and the lymphatic system, caused by
    *Staphylococcus aureus* in bacterial *endocarditis,*

*Streptococcus sanguis* in bacterial *endocarditis*,
*Staphylococcus epidermidis* in bacterial *endocarditis*
Gram-positive and Gram-negative bacteria, such as *S. aureus* and *E. coli* in intra vascular infection
*Coxsackievirus*
Rotavirus
*Murine cytomegalovirus*
Adenovirus
*Neisseria meningitides*
*Chlamydia pneumoniae*
*Wolbachia* bacteria related to Gram-negative Rickettsiales, in *Onchocerca volvulus*-infected persons
the Lyme disease spirochete *Borrelia burgdorferi*
*Coxiella burnetii*, the agent of Q fever
*Acholeplasma laidlawii*
intracellular invasion is an important aspect of Carrion's disease caused by *Bartonella Bacilliformis*. Both the hematic and tissue phases of the disease involve the initial attachment of the organism to erythrocytes and endothelial cells.
*Paracoccidioides Brasiliensis*, a dimorphic fungus known to produce invasive systemic disease in humans.

Therefore, according to the invention a composition of matter comprising negatively charged polysaccharides, optionally present in an plant or animal NAG-25 extract or in an *Aloe* ultra filter extract according to the invention, which can effectively be applied for the prevention and treatment of infections with microorganisms, presumably by prevention of the adhesion of said microorganisms. Said composition or NAG-25 extract or in an *Aloe* ultra filter extract can be applied as supplement of food and in dietary food, in personal care and in cosmetic use, and in pharmaceutical use.

The present invention will be exemplified further by the following examples which are not to be considered as restricting the scope of the invention in any way.

Materials and Methods

Materials:

Disposable polystyrene columns with maximal bed volumes of 2 ml, were obtained from Pierce, Rockford, Ireland. Sephadex G-25 Fine, DEAE-Sepharose, fast flow 5-ml desalting columns and Superose 200 HJR10/30 and 1-ml MonoQ HR 5/5 columns were purchased from Amersham Pharmacia Biotech, Uppsala, Sweden. Filtration units of 10 ml and 50 ml as well as a range of ultra filtration membranes were obtained from Amicon Corp., Lexington, USA. and Millipore, Bedford, USA. Carbopac TM MA1 and PA1 analytical columns (4×250 mm) in combination with a Carbopac TM Aminotrap Guard column (10×32 mm) and a HPAEC-PAD system were obtained from Dionex, Sunnydale, Calif., USA. Fluorotrac 600 high binding flat-bottom 96 wells microtiter plates were obtained from Greiner, Frickenhausen, Germany. High-molecular weight human salivary mucin as well as mouse anti-human monoclonal antibodies (MabF2) against salivary mucin were kindly provided by Dr. E. Veerman, Department of Oral Biochemistry, ACTA, Amsterdam. Agglutinin-enriched human saliva was a kind gift of Dr. A. J. M. Ligtenberg, Department Oral Biochemistry, ACTA, Amsterdam. Horseradish peroxidase labeled goat anti-mouse IgG and IgM were obtained from American Qualex, San Clemente, Calif., U.S.A. Fluorescein 5-isothiocyanate (FITC) was obtained from Sigma, St Louis, Mo., U.S.A.

Syto-13 green fluorescent nucleic acid stain was obtained from Molecular probes (Leiden, The Netherlands) as a 5 mM solution in dimethylsulfoxide. Standard sugars used for carbohydrate analysis were from commercial sources and of analytical grade.

*Aloe vera* Extracts:

*Aloe vera* extracts (AV-1 to AV-7, AV-15, AV-16 and AV-A to AV-F) were provided by Bioclin B.V. (Delft, the Netherlands) and originated from various commercial sources. AV-A, AV-3 and AV-4 comprise *Aloe vera* extract and gel in a ratio of 1:1, AV-B and AV-D are concentrates of commercial sources with a factor 40 and 10, respectively. AV-2 extract contains 813 and 325 µg of glucose and mannose respectively. AV-16 was prepared by ultra filtration of the filtered sap of the *Aloe vera* inner gel fillet product as described further, with a cross flow method over a hollow fiber membrane with a cut-off of 30 kD, followed by 10× concentration. AV-5, AV-6, AV-7 and AV-E were received as lyophilized powders, AV-F and AV-17 as a spray-dried powder.

All these products were *Aloe* inner gel fillet products. These gel fillets were prepared as described in CA U.S. Pat. No. 1,305,475. The processes of lyophilizing and spray-drying are known to the skilled in the art; the details differ for the various sources.

Extracts and powders were stored frozen directly after receipt; in between experiments resolubilized powders and extracts were kept at 4° C. for no longer than one month. The extracts were obtained from the leaves taken from *Aloe barbendensis* Miller. A 2% mixture of stabilisation components, consisting of ascorbic acid, sodium benzoate, potassium sorbate, tocopherol, ethyl alcohol, citric acid and sorbitol, was added directly after harvesting on the plantation. Some preparations were received as lyophilized powders which were reconstituted by the addition of milliQ-water to the desired volume. A crude preparation of Acemannan was kindly provided by dr. R. Zarzycki, Carrington Laboratories Inc. (Irving, Tex.).

Subfractionation of *Aloe vera* Extracts:

50-150 ml of *Aloe vera* extracts and reconstituted powders were centrifuged for 45 min at 15,000×g at 15° C. The pellet was discarded and the supernatant was filtered over a 0.2 µm membrane. In the routine, the resulting clear solution was optionally filtered over a small bed volume (1 ml per 5 ml) of Sephadex G-25 to remove *Aloe vera* components that had affinity for this material (Fraction III, also indicated as *Aloe vera* NAG-25 extract, see hereunder). Fraction I (apparent mol. wt >±5 kD) and II (apparent mol. wt <±5 kD) were prepared by FPLC (Åcta Explorer 10S, Amersham/Pharmacia, Uppsala, Sweden) over two coupled 5-ml desalting columns (Pharmacia) that were eluted with milliQ water at a flow rate of 5-ml/min; the absorbence was recorded at various wavelength between 190 and 280 nm. This was performed by the automated repeated injection of 0.5-ml volumes of the resulting extract and separation and collection of the two fractions on the basis of changes in conductivity, employing the AKTA Explorer 10S. Fraction II was lyophilized and subsequently solubilized into milliQ water to 0.1 of the original volume of the extract and was stored at −20° C. until use. Fraction I was passed over a DEAE-Sepharose column (prepared in milliQ water; 10 ml bed volume per 50 ml of original extract) and washed with 2 column volumes of milliQ water to collect the non-retarded (I-$D_0$) and weakly retarded (I-$D_W$) fractions. Bound materials (I-$D_f$) were eluted with 1 column volume of 0.5 M NaCl in milliQ water. Fraction I-$D_0$ was concentrated to 0.1 of the original volume of the *Aloe vera* extract by ultra filtration, under nitrogen pressure, through a PM10 membrane using a 10- or 50-ml filtration unit. Fraction I-$D_f$ was desalted by the automated procedure described above and subsequently was concentrated to 0.1 of the original volume of the *Aloe vera* extract by ultrafiltration over a PM-10 filter. In some experiments, subfractions with apparent molecular weights of >300, 100-300, 50-100 and 10-50 kD were prepared from Fractions I-D$_0$ and I-D$_I$ by sequential ultra filtration, respectively, over a XM-300, XM-100, XM-50 and finally a PM-10 membrane. Alternatively, comparable subfractions were prepared by preparative FPLC over a Superose 200 HR 10/30. Each subfraction was washed 3 times by adding milliQ water to 10 times the final volume obtained; the first wash was added to the subsequent fraction prior to filtration over the next filter. All fractions were stored in aliquots at −20° C. until further use.

*Aloe vera* NAG-25 Extract:

10 gram spray dried *Aloe vera* spray dried extract originating from 2 liter *Aloe vera* extract was solubilized in 200 ml Milli-Q water and passed over a Sephadex G-25 column (5 cm wide and 10 cm high; prepared in Milli-Q water; flow rate 7.5 ml/min) to remove materials that have affinity for the Sephadex G-25 matrix and reduce the content of low molecular weight molecules. The column is subsequently washed with Milli-Q water and the *Aloe vera* NAG-25 extract is collected as the 60-310 ml eluate.

Bacteria and Bacterial Extracts:

Wildtype *H. pylori* (ATCC 43504) was grown under micro aerophilic conditions on blood agar DENT plates as described by F. Namavar et al., Infection Immunity, 66, 444-447 (1998)]. *Helicobacter pylori* extracts containing the adhesins of the outer membrane, the so-called S-layer, were prepared from confluent bacterial cultures from two or more agar plates. The bacteria were suspended in 0.15 M NaCl, vortexed for 1 min. and centrifuged for 30 min at 5000×g. The supernatant containing the bacterial extract was stored at −80° C. after determination of the protein concentration by the BCA protein assay (Pierce, Rockford, USA). FITC-labelled *H. pylori* were prepared by incubating bacteria in 1 ml 0.2 M carbonate buffer (pH 8.0) containing 0.1 mg/ml FITC for 15 min in the dark at albumin (PBST-BSA), the cells were suspended in the same buffer at a density on 0.13-0.20 A$_{600\,nm}$ units and were stored in 0.1-ml aliquots until used.

Bacterial cultures of *Psuedomonas aeruginosa* strains PA025 and PA14 were obtained from the Department of Medical Microbiology, VU medical centre and of *Streptococcus mutans* and *Streptococcus sanguis* were obtained from the Department Oral Biochemistry, ACTA, Amsterdam. In case the bacteria were used in a fluorescent inhibition assays, the bacteria were suspended and diluted in 100 mM sodium acetate (pH 5), containing 0.5% Tween-20 to a final absorbance at 700 nm of 0.1. The bacteria were fluorescent labelled by the addition of Syto-13 (1:500 v/v).

Fluorescent Inhibition Assay.

Fluotrac 600 plates were coated with a dilution range of salivary mucin (for *H. pylori* and *Pseudomonas aeruginosa*) or agglutinin-enriched human saliva (for *Streptococcits mutans* and *Streptococcus sanguis*) in coating buffer (0.1 M sodium carbonate (pH 9.6)). The plates were incubated overnight at 4° C. and subsequently washed 4 times with PBS-0.1% Tween-20 (washing buffer). Syto-13 labelled bacteria (50 µL) were added to the wells followed by 50 µL of a dilution of an *Aloe vera* I-D$_I$ sample or water (positive control). Wells without coated mucin served as a negative control. After incubation for 1 h at 37° C. the plates were washed with washing buffer. The fluorescence was measured with the Fluostar Galaxy, excitation and emission wavelength were respectively 485 and 520 nm.

Monosaccharide Analysis:

Analysis of monosaccharides was performed by high pH anion-exchange chromatography with pulsed amperometric detection (HPAEC-PAD) on a Carbopack TM MAI column after hydrolysis of the fractions for 4 h in 2 M tri fluoroacetic acid at 100° C. The column was eluted with 0.2 M NaOH at a flow rate of 0.4 ml/min and was calibrated with a mixture of standard sugars.

EXAMPLE 1

Inhibition of Adherence of *H. pylori* to Salivary Mucin

Inhibition of the binding of *H. pylori* adhesin to human salivary mucin by *Aloe vera* extracts or subfractions was studied by an established ELISA (see F. Navamar et al., indicated above), in which microtiter plates coated with a S-layer preparation of *Helicobacter pylori* (100 µl/well; 10-20 µg protein/ml; 16 h at 4° C.; washing buffer PBS (pH 7.5)-0.1% Tween-20 (v/v) (PBST)) were incubated in duplicate with human salivary mucin in the presence and absence of dilution ranges of *Aloe vera* extracts or fractions in for 2 h at 37° C. The total volume of the incubation mixtures was 100 µl, which was composed of 50 µl of salivary mucin (0.2-0.5 µg/ml) and 50 µl of a dilution of *Aloe vera* sample both in 50 mM sodium acetate-150 mM NaCl-0.5% Tween-20 (pH 5.0). The monoclonal antibody F2, recognizing the sulfo-Lewis$^a$ groups expressed on the salivary mucin, and peroxidase-labeled goat-ante mouse antibodies were used for detection of the amount of bound mucin after being washed with PBST as described earlier, for instance by E. Veerman et al., Glycobiology 7, 737 (1997).

Samples were tested in duplicates in a 2-fold dilution range. The inhibitory activity was expressed as the percentage decrease of A$_{490\,nm}$ relative to control wells containing only mucin after correction for the reagent blank. The results are given in the FIGS. 2 and 3 and in table 1. As described above the inhibitory activities of the DEAE-binding fractions are much higher than of the non-binding fractions. From this DEAE-binding fraction the 100-300 kD subfraction expresses the highest inhibitory activity (82%).

EXAMPLE 2

Inhibition of Adherence of *H. pylori* to Gastric Mucosa

Adherence of FITC-labeled bacteria to gastric antrum sections was detected according to Boren et al, see above. Six-µm sequential slices of human gastric antrum, derived from normal tissue and from patients with slightly and moderately inflamed and metaplastic tissue were provided by the Department of Pathology. Sequential slices were de paraffinized in xylene (10 min, 3 times rinsing), followed by washing 3 times for 5 min ethanol, rehydration in slowly running milliQ water and washing 3 times for 5 minutes in PBS. A circle was drawn around the slices with a PAP pen PA03 (Diagnostics BV, Uithoom, The Netherlands) followed by incubation with 0.1 ml PBST-BSA under humid conditions, for at least 1 hr at 4° C. Finally, the buffer was replaced by 0.1 ml of FITC-labelled bacteria plus or minus (positive control) a dilution range of the AV-5 extract or subfraction in PBST-BSA. The slides were incubated for 1 hr in the dark. Unbound bacteria were removed by washing 6 times with PBST-BSA on a rotating table. Finally, PBS in glycerol (1:1 v/v) was applied to the sections before sealing them with a cover glass for fluorescence microscopy using a Nikon Eclipse microscope (Uvikon, Bunnik, The Netherlands), with a Nikon digital camera DxM 1200 and the Nikon ACT-1 camera control program.

The results are given in FIG. 4. Controls without *Aloe vera* subfractions were identical to plate c (not shown). As described above the total weight fraction I of an *Aloe vera* extract strongly inhibited the adherence of bacteria to the mucosa (see FIG. 4b) while this inhibition was reduced to almost zero when the uncharged fraction alone is co-incubated with the FITC-labelled bacteria.

EXAMPLE 3

Inhibition of Adherence of *H. pylori* on MUC5-Labelled Multi-Well Plates

In the fluorescent inhibition assay life bacteria, of which the DNA has been labelled with the fluorescent dye Syto-13, are incubated in the presence or absence of an *A. vera* I-$D_I$ preparation in a 96-well plate coated with the indicated dilutions of salivary mucin MUC-5 or agglutinin-enriched saliva. In each well the same amount of Syto-13-labelled bacteria were present. Per experiment, all wells contained the same amount of the *A. vera* preparation in case of co-incubation with bacteria All assays were performed in duplicate.

Typical experiments are shown in tables 2 and 3. The extent of binding of life *Helicobacter pylori* to the wells was clearly dependent of the amount of coated MUC-5 present on the wells. Co-incubation with the I-$D_I$-preparation inhibited the binding of *Helicobacter pylori* to MUC-5 in a concentration-dependent way. The inhibition increased when the amount of MUC-5 decreased (Experiment 1) and also when more I-$D_I$ was added (Experiment 2). The amount of material in 0.01 ml I-$D_I$ present in the wells was derived from 0.02 g of AV-17 powder (corresponding to 10-20 ml original *A. vera* gel).

EXAMPLE 4

Inhibition of Adherence of Syto-13 Labelled *Pseudomonas aeruginosa* on MUC5-Labelled Multi-Well Plates The effects of an AV-16 I-$D_I$ preparation were tested on two strains of *P. aeruginosa, P. aeruginosa* PA025 and *P. aeruginosa* PA14. The amount of material in 0.01 ml AV-16 I-$D_I$ fraction was derived from 2.5 ml AV-16. The amount of bacteria bound to the plates was dependent on the amount of coated MUC-5. The results were given in table 4 and table 5, respectively. Co-incubation with 0.01 ml of AV-16 I-$D_I$ resulted in a strong inhibition of the binding of the bacteria. The pilot study suggests that the inhibition is concentration dependent since the inhibition increased when the amount of coated MUC-5 decreased.

EXAMPLE 5

Inhibition of Adherence of Syto-13 Labelled *S. mutans* and *S. sanguis* on Agglutinin-Enriched Saliva Coated to the Plates The effects of an AV-16 I-$D_I$ preparation were tested on two strains of *Streptococcus mutans* and *Streptococcus sanguis*. The amount of bacteria bound to the plates was dependent on the amount of agglutinin-enriched saliva coated to the plates. Co-incubation with 0.01 ml of AV-16-D1 resulted in a strong inhibition of the binding of the bacteria. The amount of material in 0.01 ml AV-16-D1 was derived from 2.5 ml *Aloe vera* 16.

The invention claimed is:
1. A composition, consisting essentially of:
 isolated polysaccharides derived from *Aloe vera* wherein:
 a) the polysaccharides comprise 60-90% D-mannose, 30-10% D-glucose and 0-10% other monosaccharides and the ratio of D-mannose and D-glucose in said polysaccharide is about 5:1 to 20:1;
 b) the polysaccharides are negatively charged;
 c) the polysaccharides bind to a positively charged column; and
 d) the polysaccharides have an average molecular weight higher than 50 kD, wherein said composition prevents microbial adhesion to tissues.
2. The composition according to claim 1, wherein:
 a) the polysaccharides comprise 70-90% D-mannose, 30-10% D-glucose and 0-10% other monosaccharides
 b) the polysaccharides are negatively charged
 c) the polysaccharides bind to a positively charged column.
3. The composition according to claim 1, wherein said polysaccharides have an average molecular weight of about 100-300 kD.
4. An ultrafiltration aloe extract comprising the composition according to claim 1.
5. A food supplement or dietary food, comprising the composition according to claim 1.
6. A cosmetic product comprising the composition according to claim 1.
7. A pharmaceutical composition comprising the composition according to claim 1.
8. An anti-bacterial, anti-viral or anti-inflammatory pharmaceutical comprising the composition according to claim 1.
9. An oral dosage form selected from the group consisting of tablet, capsule and syrup comprising the composition according to claim 1.
10. A topical dosage form selected from the group consisting of cream and gel comprising the composition according to claim 1.
11. An injectable dosage comprising the composition according to claim 1.
12. A composition, consisting of:
 an isolated, negatively-charged polysaccharides fraction from *Aloe vera*, the fraction being able to bind to a positively charged column, wherein
 the polysaccharides comprise 70-90% D-mannose, 30-10% D-glucose and 0-10% other monosaccharides,
 the ratio of D-mannose and D-glucose in the polysaccharides is about 5:1-20:1, and
 the polysaccharides have an average molecular weight of about 100-300 kD, wherein said composition prevents microbial adhesion to tissues.

* * * * *

UNITED STATES PATENT AND TRADEMARK OFFICE
CERTIFICATE OF CORRECTION

PATENT NO. : 8,628,807 B2  Page 1 of 1
APPLICATION NO. : 10/500390
DATED : January 14, 2014
INVENTOR(S) : Van Dijk et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 393 days.

Signed and Sealed this
Twenty-second Day of September, 2015

Michelle K. Lee
*Director of the United States Patent and Trademark Office*